United States Patent
Chen

(10) Patent No.: US 8,911,814 B2
(45) Date of Patent: Dec. 16, 2014

(54) MEDICAL DEVICE COATING CONFIGURATION AND METHOD FOR IMPROVED LUBRICITY AND DURABILITY

(75) Inventor: Hancun Chen, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 341 days.

(21) Appl. No.: 12/976,695

(22) Filed: Dec. 22, 2010

(65) Prior Publication Data

US 2011/0091639 A1   Apr. 21, 2011

Related U.S. Application Data

(63) Continuation of application No. 11/509,210, filed on Aug. 24, 2006, now Pat. No. 7,857,008.

(51) Int. Cl.
 *A61L 33/00* (2006.01)
 *A61M 25/09* (2006.01)

(52) U.S. Cl.
 CPC ..................................... *A61M 25/09* (2013.01)
 USPC .......... 427/2.1; 427/2.24; 427/230; 427/2.25; 427/180; 427/189; 623/1.13; 623/1.11; 623/1.15

(58) Field of Classification Search
 CPC ................................. A61L 33/00; A61F 2/06
 USPC ................ 427/2.24, 2.1, 230, 2.25, 180, 189; 623/1.11
 See application file for complete search history.

(56) References Cited

U.S. PATENT DOCUMENTS

| | | |
|---|---|---|
| 3,390,546 A | 7/1968 | Jewel |
| 4,580,551 A | 4/1986 | Siegmund et al. |
| 4,639,252 A | 1/1987 | Kelly et al. |
| 5,106,455 A | 4/1992 | Jacobsen et al. |
| 5,201,723 A | 4/1993 | Quinn |
| 5,325,845 A | 7/1994 | Adair |
| 5,507,751 A | 4/1996 | Goode et al. |
| 5,569,197 A | 10/1996 | Helmus et al. |
| 5,573,520 A | 11/1996 | Schwartz et al. |
| 5,741,429 A | 4/1998 | Donadio, III et al. |
| 5,772,609 A | 6/1998 | Nguyen et al. |
| 6,139,510 A | 10/2000 | Palermo |
| 6,428,489 B1 | 8/2002 | Jacobsen et al. |
| 6,766,720 B1 | 7/2004 | Jacobsen et al. |
| 6,786,876 B2 | 9/2004 | Cox |
| 2002/0013540 A1 | 1/2002 | Jacobsen et al. |
| 2002/0065553 A1 | 5/2002 | Weber |
| 2003/0069522 A1 | 4/2003 | Jacobsen et al. |
| 2004/0181174 A2 | 9/2004 | Davis et al. |
| 2004/0213893 A1* | 10/2004 | Boulais ........................ 427/2.24 |
| 2005/0267444 A1 | 12/2005 | Griffin et al. |
| 2006/0047224 A1 | 3/2006 | Grandfield |
| 2006/0241564 A1 | 10/2006 | Corcoran et al. |
| 2007/0112331 A1 | 5/2007 | Weber et al. |
| 2007/0113912 A1 | 5/2007 | Lawrence |
| 2008/0097397 A1 | 4/2008 | Vrba |
| 2008/0125753 A1 | 5/2008 | Chen et al. |

* cited by examiner

*Primary Examiner* — Dah-Wei D Yuan
*Assistant Examiner* — Andrew Bowman
(74) *Attorney, Agent, or Firm* — Seager, Tufte & Wickhem, LLC

(57) ABSTRACT

Medical devices and methods for making and using the same. An example medical device includes a slotted tubular member and a coating disposed over the tubular member. The coating may define one or more coating gaps therein.

19 Claims, 6 Drawing Sheets

MEDICAL DEVICE COATING CONFIGURATION AND METHOD FOR IMPROVED LUBRICITY AND DURABILITY

RELATED APPLICATIONS

This application is a continuation of co-pending U.S. application Ser. No. 11/509,210, filed Aug. 24, 2006, the entire disclosure of which is incorporated herein by reference.

FIELD OF THE INVENTION

The present invention pertains to intracorporeal medical devices, for example, intravascular guidewires, catheters, stents, and the like as well as improved methods for manufacturing medical devices. More particularly, the invention relates to medical devices with coatings.

BACKGROUND

A wide variety of intracorporeal medical devices have been developed for medical use, for example, intravascular use. Some of these devices include guidewires, catheters, stents, and the like. Of the known medical devices, each has certain advantages and disadvantages. There is an ongoing need to provide alternative medical devices as well as alternative methods for manufacturing medical devices.

BRIEF SUMMARY

The invention provides design, material, and manufacturing method alternatives for medical devices. An example medical device includes a slotted tubular member and a coating disposed over the tubular member. The coating may define one or more coating gaps therein.

The above summary of some embodiments is not intended to describe each disclosed embodiment or every implementation of the present invention. The Figures and Detailed Description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

Figure 1:
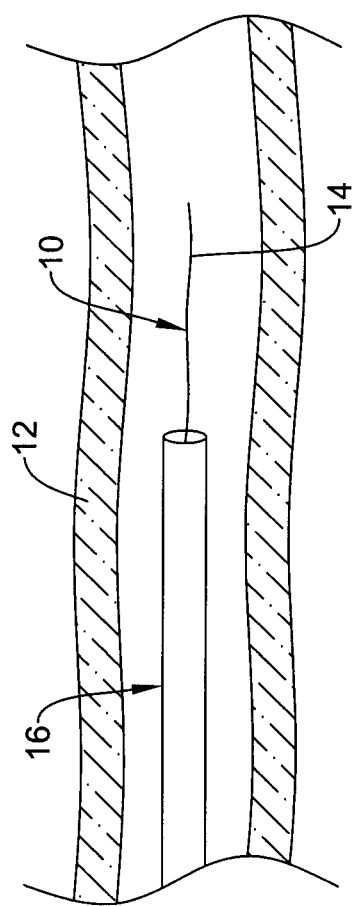
FIG. 1 is a plan view of an example medical device disposed in a blood vessel.

FIG. 1 is a plan view of an example guidewire 10 disposed in a blood vessel 12. Guidewire 10 may include a distal section 14 that may be, as is well known in the art, generally configured for probing deep within the anatomy of a patient. Guidewire 10 may be used for intravascular procedures according to common practice and procedure. For example, guidewire 10 may be used in conjunction with another medical device such as a catheter 16. Of course, numerous other uses are known amongst clinicians for guidewires and other similarly configured medical devices.

Figure 2:
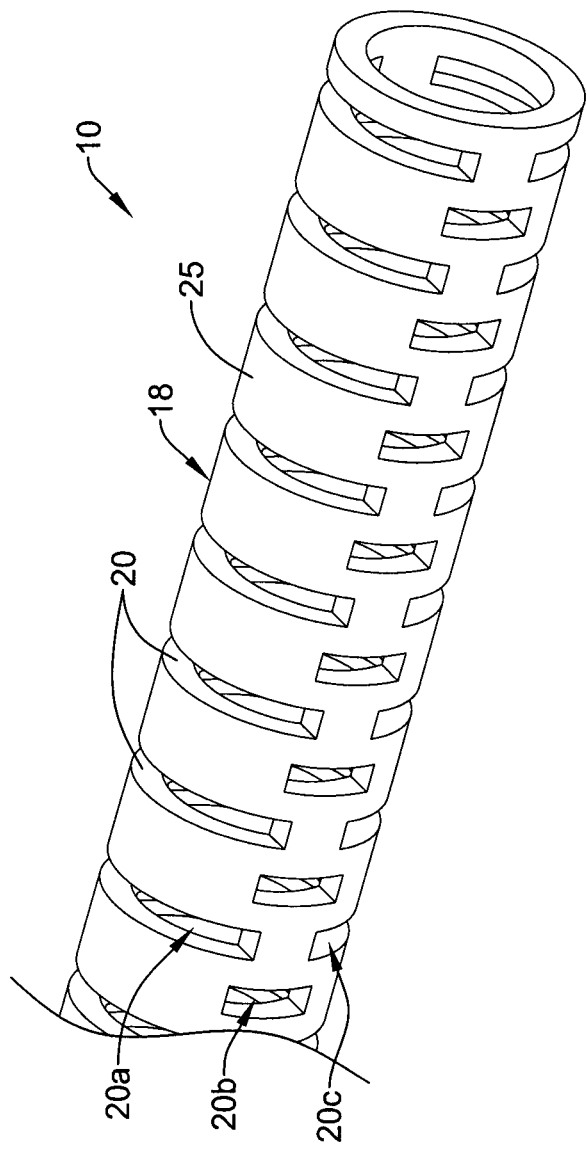
FIG. 2 is a perspective view of a portion of an example medical device.

Turning now to FIG. 2, here it can be seen that guidewire 10 may include a tubular member 18 having a plurality of slots 20 formed therein. Tubular member 18 may be made of a metal, metal alloy, polymer, metal-polymer composite, or any other suitable material. Some examples of suitable metals include stainless steel, such as 304V, 304L, and 316LV stainless steel; mild steel; nickel-titanium alloy such as linear-elastic or super-elastic nitinol, nickel-chromium alloy, nickel-chromium-iron alloy, cobalt alloy, tungsten or tungsten alloys, MP35-N (having a composition of about 35% Ni, 35% Co, 20% Cr, 9.75% Mo, a maximum 1% Fe, a maximum 1% Ti, a maximum 0.25% C, a maximum 0.15% Mn, and a maximum 0.15% Si), hastelloy, monel 400, inconel 825, or the like; other Co—Cr alloys; platinum enriched stainless steel; or other suitable material. In general, the materials chosen for tubular member 18 provide tubular member 18 (and/or guidewire 10) with a number of desirable characteristics. For example, materials such as nickel-titanium alloys may provide a desirable level of flexibility and torque-transmitting characteristics that may help guidewire 10 be suitable for a number of different interventions.

Slots 20 may be micromachined or otherwise created in tubular member 18, and may be configured to make tubular member 18 more flexible in bending. It is worth noting that, to the extent applicable, the methods for forming slots 20 can include, for example, any of the appropriate micromachining methods disclosed herein or any of micromachining and other cutting methods disclosed in U.S. Pat. Publication No. 2003/0069522A1 and/or U.S. Pat. No. 6,766,720, the entire disclosures of which are herein incorporated by reference. These and other cutting methods may also include saw cutting (e.g., diamond grit embedded semiconductor dicing blade), etching (for example using the etching process described in U.S. Pat. No. 5,106,455, the entire disclosure of which is herein incorporated by reference), laser cutting, electron discharge machining, or the like. It should be noted that the method for manufacturing guidewire 10 may include forming slots 20 in tubular member 18 using any of these or another manufacturing step.

Various embodiments of arrangements and configurations of slots 20 are contemplated. Slots 20 are generally arranged to be perpendicular to the longitudinal axis of tubular member 18. This arrangement can, alternatively, be described as having slots 20 lying within a plane that is normal to the longitudinal axis of tubular member 18. In some embodiments, slots 20 may be formed part way through tubular member 18, while in other embodiments, slots 20 may extend all the way through tubular member 18. Any one or more of the individual slots 20 may extend only partially around the longitudinal axis of tubular member 18. Slots 20 may be formed in groups of two, three, or more slots 20, which may be located at substantially the same location along the axis of tubular member 18, and may be substantially perpendicular to the longitudinal axis.

Figure 3:
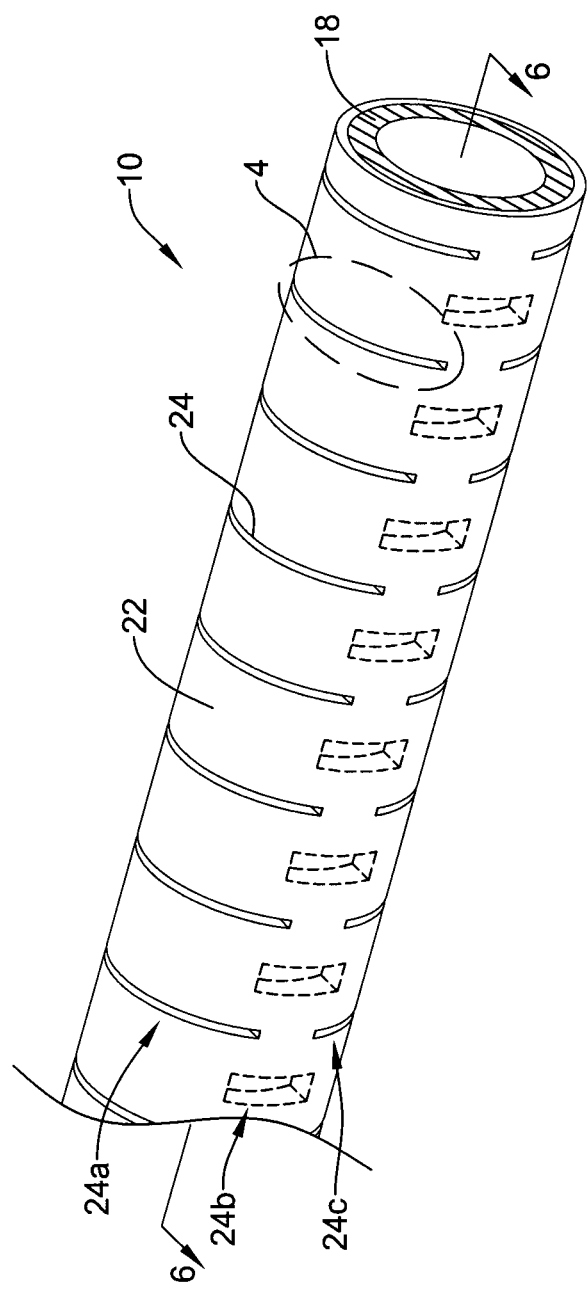
FIG. 3 is a perspective view of the portion of the example medical device shown in FIG. 2 with a coating disposed thereon.

A coating or coating material 22, such as a polymeric coating, may be disposed on the outer surface of tubular member 18 as shown in FIG. 3. Coating 22 may be a lubricious, a hydrophilic, a hydrophobic, a protective, a medicated, or other type of coating. Suitable materials for coating 22 may include silicone, polysulfones, polyfluorocarbons (such as TEFLON), polyolefins such as polyethylene, polypropylene, polyesters (including polyamides such as nylon), polyurethanes, polyarylene oxides, polyvinylpyrolidones, polyvinylalcohols, hydroxyl alkyl cellulosics, algins, saccharides, caprolactones, and the like, and mixtures and combinations thereof. Any other suitable polymer may also be utilized without departing from the spirit of the invention.

In some embodiments, coating 22 may be a single, homogeneous layer of a single polymer. Alternatively, coating 22 may include a homogenous or non-homogenous blend of polymers. For example, coating 22 may differ in composition along the length of guidewire 10. In other embodiments, coating 22 may have multiple layers of the same, different, or blended polymers that are either homogeneously or non-homogeneously arranged. Other embodiments include materials that are blended among themselves or with formulated amounts of water insoluble compounds (including some polymers) to yield coatings with suitable lubricity, bonding, and solubility. Some other examples of such coatings and materials used to create such coatings can be found in U.S. Pat. Nos. 6,139,510 and 5,772,609, which are incorporated herein by reference.

Coating 22 may be made from, doped with, or otherwise include a radiopaque material. Radiopaque materials are understood to be materials capable of producing a relatively bright image on a fluoroscopy screen or another imaging technique during a medical procedure. This relatively bright image aids the user of guidewire 10 in determining its location. Some examples of radiopaque materials can include, but are not limited to, gold, platinum, molybdenum, palladium, tantalum, tungsten or tungsten alloy, plastic material loaded with a radiopaque filler, and the like.

Because tubular member 18 is often designed with particular flexibility and torque-transmitting characteristics in mind, for example, it may be desirable to apply coating 22 to tubular member 18 in a manner that compliments, has the desired (and sometimes minimal) impact on, or further refines these characteristics. For example, tubular member 18 may be designed to be highly flexible, for example for probing deep within the vasculature, and coating 22 may be disposed on tubular member 18 in a manner that has a minimal or predictable impact on the flexibility of tubular member 18.

In at least some embodiments, coating 22 may be configured to have one or more coating gaps 24 formed therein. Coating gaps 24 are generally arranged in a manner that has the desired effect (or "non-effect") on the flexibility of tubular member 18. For example, coating gaps 24 may be disposed over some or all of slots 20. These arrangements may, for example, allow tubular member 18 to remain highly flexible by reducing the amount of coating material 22 disposed at slots 20.

Figure 4:
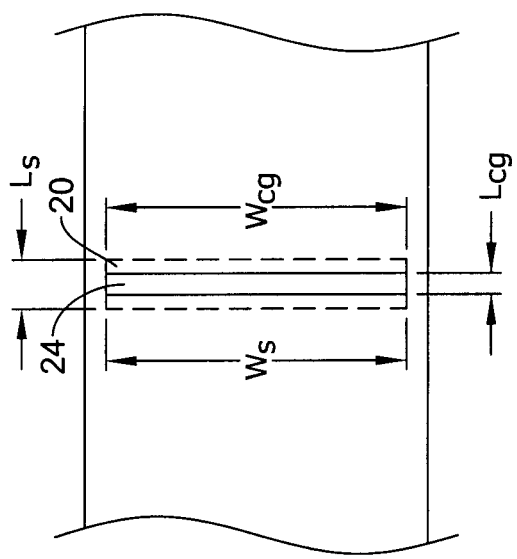
FIG. 4 is a side view of an example coating gap.

The manner in which coating gaps 24 are disposed over slots 20 may further allow tubular member 18 to be flexible. For example, the coating gaps 24 may have a length $L_{cg}$ that may be shorter than a length $L_s$ of the slots 20 as shown in FIG. 4. In addition, coating gaps 24 may have a width $W_{cg}$ that may be the substantially the same as a width $W_s$ of slots 20 as seen in FIG. 4. This arrangement may desirably impact the flexibility of tubular member 18 as described in more detail below. In alternative embodiments, $L_{cg}$ may be substantially the same or longer than $L_s$ and/or $W_{cg}$ may be longer or shorter than $W_s$. It should be noted that any of these configurations can be analogously applied to embodiments where slots 20 have a major axis that extends in the longitudinal direction.

As seen in FIG. 4, the $W_{cg}$ is generally longer than $L_s$. In some embodiments, $W_{cg}$ can be about 1.5 to about 500 times longer than $L_s$. In other embodiments, $W_{cg}$ can be about 1.5, 2, 2.5, 3, 3.5; 4, 4.5, 5, or more times longer than $L_s$. However, this need not be the case as the relative lengths/widths can vary on a number of factors including the shape of slots 20. For example, slots 20 as shown in FIG. 2, generally have a long axis that lies in a plane that is normal to the longitudinal axis of tubular member 18. Other embodiments are contemplated, for example, where slots 20 have a long axis that lies longitudinally aligned with the longitudinal axis of tubular member 18. In these embodiments, $L_s$ may be longer than $W_{cg}$ at proportions similar to what is described above or any other suitable arrangement.

In at least some embodiments, coating gaps 24 can be seen as being longitudinally shorter but yet laterally or circumferentially just as wide as slots 20. Because coating gaps 24 may be just as wide as slots 20, coating 22 may be more durable and resilient while still being able to provide a suitable "coating" (e.g., lubricious, hydrophobic, or other coating) to tubular member 18. In addition, because coating gaps 24 may be longitudinally shorter than slots 20, not only is coating 22 more durable and resilient by virtue of this arrangement, coating gaps 24 define a space extending in the circumferential direction about tubular member 18 and over slots 20 that allows for lateral deflections in tubular member 18 to occur without having to overcome significant resistance created by the presence of coating material 22 adjacent or within slots 20 (e.g., where tubular member 18 may be bending).

In addition, combinations of the aforementioned arrangement with alternative arrangements may allow for differing flexibility characteristics. For example, some embodiments of tubular member 18 include slots 20 arranged in longitudinal rows, for example, as indicated in FIG. 2 as a first slot row 20a, a second slot row 20b, and a third slot row 20c. Coating gaps 24 may be similarly arranged in longitudinal rows, for example, as indicated in FIG. 3 as a first gap row 24a, a second gap row 24b, and a third gap row 24c. Some embodiments of guidewire 10 are contemplated that utilize one or more rows of coating gaps 24 (e.g., row 24a, row 24b, row 24c, or combinations thereof) disposed over one or more rows of slots 20 (e.g., row 20a, row 20b, row 20c, or combinations thereof). For example, some embodiments include row 24a of coating gaps 24 disposed over row 20a of slots 20. One or more of the remaining rows 20b/c of slots 20 may be free of coating gaps 24. For example, FIGS. 2/3 illustrates that row 20b of slots 20 is free of coating gaps 24 in row 24b. This particular arrangement may decrease the flexibility (e.g., stiffen) along rows 20b and define guidewire 10 as having a favored or more flexible bending direction (e.g., laterally in a direction that is perpendicular to row 20a and/or row 24a). Similarly, some embodiments includes two rows 24a/c of coating gaps 24 disposed over two rows 20a/c of slots 20. Analogously, this arrangement may result in a zone of flexibility or plurality of favored or more flexible bending directions along rows 20a/c and/or rows 24a/c and a stiffened region along row 20b and/or 24b.

In addition to the aforementioned desirable characteristics associated with having coating gaps 24 in coating 22, a number of additional advantages are contemplated. For example, the inclusion of coating gaps 24 may help to smooth out the exterior of guidewire 10, thereby improving the lubricity and handling of guidewire 10. Additionally, the presence of coating gaps 24 across slots 20 allows for guidewire 10 to bend freely over slots 20 when force is applied. Because coating 22 is discontinuous over slots 20, the amount of chipping of coating material 22 at, for example, the edges of slots 20 is reduced. In addition, the methods for applying coating 22 and defining coating gaps 24 allow for coating 22 to be applied to tubular member 18 without the need of a bonding or tie layer. This may help to reduce the manufacturing cost of guidewire 10.

The process for applying coating 22 to tubular member 18 may include any suitable method such as dip coating, spraying, and the like. Defining coating gaps 24 in coating 22 may include a wide variety of methods. For example, coating material 22 may be dissolved, suspended in, or otherwise mixed with a solvent that can be subsequently removed (e.g., by evaporation or any other suitable manner) to leave coating gaps 24. Some examples of solvents include water (such as deionized water), alcohol (e.g., isopropyl alcohol (IPA) and ethyl alcohol), ethers (e.g., methanol, propanol, isopropanol, and ethanol), toluene, N-methyl-2-pyrrolidone (NMP), tetrahydrofuran, methylene dichloride, methylethylketone, dimethylacetate, ethyl acetate, and their mixtures and combinations thereof. It should be noted that the word "solvent" is used herein for convenience and is not intended to limit the invention to any particular class or kind of material.

In at least some embodiments, the solvent acts like a "mask" or masking agent/solution that, in a sense, blocks a portion of coating 22 such that when the masking solution is removed, a newly defined coating gap 24 is left behind. Removing the solvent or masking agent may include removing the solvent over a particular slot 20, a particular row or rows of slots 20, all of slots 20, at a location away from slots 20, or combinations thereof. The process of removing the solvent the may include curing the coating 22. For example, an oven (or other chamber used for heating and/or drying) may be used to cure the coating 22 and/or evaporate or dissipate the solvent. In some embodiments, ultraviolet (UV) light sources or other radiation sources may be used to cure the coating 22 and/or evaporate or dissipate the solvent. Alternatively, the solvent may be removed by dissipation through evaporation (e.g., at room temperature) and/or expulsion such as with a vacuum or other expulsion means. Some additional details regarding this masking-solution dipping methodology can be found in U.S. application Ser. No. 11/509,204, filed Aug. 24, 2006 and entitled "ELONGATE MEDICAL DEVICE AND METHOD OF COATING THE SAME", the disclosure of which is herein incorporated by reference.

Figure 5:
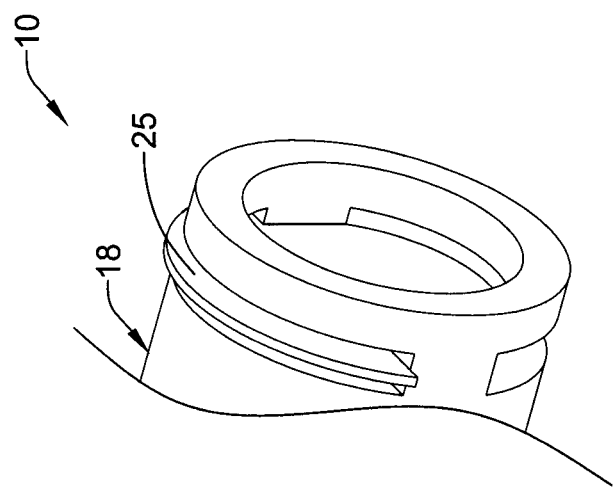
FIG. 5 is a perspective view of a tubular member with an example masking member disposed therein.

Alternatively, the "masking agent" may include a structural barrier disposed adjacent tubular member 18 in order to physically define coating gaps 24. Turning now to FIG. 5, here it can be seen that one or more masking members 25 may disposed within tubular member 18 and project through one or more slots 20. Because masking member 25 extends outward beyond the outer surface of tubular member 18, application of coating 22 to tubular member 18 can be performed in a manner such that coating 22 does not cover masking member 25 or is otherwise removable from masking member 25. Thus, once coating material 22 is suitably dried and/or cured, masking member 25 can be removed, leaving behind newly defined coating gaps 24.

In still other embodiments, coating gaps 24 can be defined by a suitable cutting and/or heating method. For example, coating gaps 24 may be defined by laser cutting portions of coating 22 at the desired location.

Figure 6:
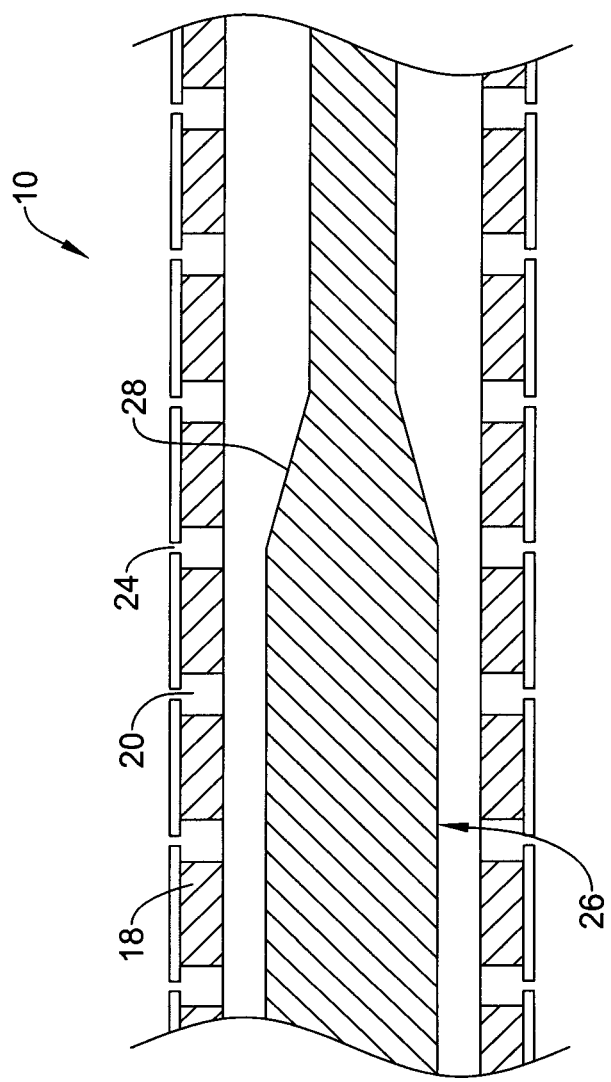
FIG. 6 is a cross-sectional view taken through line 6-6 in FIG. 3.

Turning now to FIG. 6, here it can be seen that, in addition to tubular member 18, coating 22, and coating gaps 24, guidewire 10 include other structures such as those commonly associated with guidewires. For example, guidewire 10 may include a core wire 26. Core wire 26 may be disposed within a portion of tubular member 18. In some embodiments, core wire 26 may include one or more tapers or tapered regions 28. Guidewire 10 may also include other structures common to guidewires such as a polymeric tip, a spring tip, one or more radiopaque markers, and the like. The materials utilized for these structures and other analogous structures may include those disclosed herein or any other suitable material.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A method for coating at least a portion of a medical device, the method comprising:
   providing an elongate medical device, the medical device including an elongate core member having a proximal end region and a distal end region and a tubular member disposed over the distal end region, the tubular member having an outer surface and a plurality of slots formed along the outer surface;
   masking a portion of the tubular member adjacent at least one of the slots with a masking agent, wherein the masking agent is a structural barrier positioned within the tubular member and a portion of the masking agent projects through one or more of the plurality of slots, is spaced apart from sidewalls of the slots, and extends outward beyond an outer surface of the tubular member;
   coating the tubular member with a coating material; and
   removing the masking agent, wherein a coating gap is defined in the coating material at a location corresponding to the position of the masking agent.

2. The method of claim 1, wherein coating the tubular member with a coating material includes dip coating.

3. The method of claim 2, wherein dip coating includes dipping the tubular member into a hydrophilic polymer.

4. The method of claim 1, wherein coating the tubular member with a coating material includes spray coating.

5. The method of claim 1, wherein the masking agent is a solvent.

6. The method of claim 1, wherein masking a portion of the tubular member adjacent at least one of the slots with a masking agent includes masking each of the slots.

7. The method of claim 1, wherein the slots are arranged into two or more longitudinally-aligned rows and wherein masking a portion of the tubular member adjacent at least one of the slots with a masking agent includes masking a single longitudinally-aligned row of slots.

8. The method of claim 1, wherein the slots are arranged into three or more longitudinally-aligned rows and wherein masking a portion of the tubular member adjacent at least one of the slots with a masking agent includes masking at least two of the longitudinally-aligned rows of slots.

9. The method of claim 1, wherein the coating gaps have a width and a length and wherein the width is longer than the length.

10. The method of claim 9, wherein the width is about 1.5 to about 500 times longer than the length.

11. The method of claim 9, wherein the coating gaps are disposed over at least some of the slots, wherein the slots have a width, and wherein the width of the coating gaps substantially spans the width of the slots.

12. The method of claim 9, wherein the slots having a length and wherein the length of the coating gaps is less than the length of the slots.

13. A method for coating a medical device, the method comprising:
    providing an elongate core member having a proximal end region and a distal end region and a tubular member disposed over the distal end region, the tubular member having a plurality of slots formed therein;
    providing a masking member, wherein the masking member is a structural barrier positioned within the tubular member and a portion of the masking member projects through one or more of the plurality of slots and is spaced apart from sidewalls of the slots and extends outward beyond an outer surface of the tubular member;
    arranging the masking member so that the masking member extends through at least some of the slots;
    coating an outer surface of the tubular member with a coating material;
    removing the masking member from the tubular member; and
    wherein removing the masking member defines a coating gap in the coating material.

14. The method of claim 13, wherein the coating gaps have a width and a length and wherein the width is longer than the length.

15. The method of claim 14, wherein the slots having a length and wherein the length of the coating gaps is less than the length of the slots.

16. The method of claim 13, wherein the tubular member has a longitudinal axis and wherein at least some of the slots lie in a plane that is substantially normal to the longitudinal axis.

17. The method of claim 13, wherein coating an outer surface of the tubular member includes dip coating.

18. The method of claim 13, wherein arranging the masking member so that the masking member extends through at least some of the slots includes arranging the masking member so that the masking member extends through all of the slots.

19. A method for manufacturing a medical device, the method comprising:
    providing an elongate core member having a proximal end region and a distal end region and a tubular member disposed over the distal end region, the tubular member having a plurality of slots formed therein;
    wherein the tubular member has an outer surface and an interior lumen;
    wherein at least some of the slots have a longitudinal length and a width that is greater than the longitudinal length;
    providing a masking member, wherein the masking member is a structural barrier positioned within the tubular member and a portion of the masking member projects through one or more of the plurality of slots and is spaced apart from sidewalls of the slots and extends outward beyond an outer surface of the tubular member;
    wherein the masking member includes a first portion configured to extend within the interior lumen of the tubular member and a second portion configured to extend through one or more of the slots;
    arranging the masking member so that the first portion is disposed within the interior lumen of the tubular member and so that the second portion extends through at least one of the slots;
    coating the outer surface of the tubular member with a coating material;
    removing the masking member from the tubular member; and
    wherein removing the masking member defines a coating gap in the coating material.

* * * * *